US00RE48867E

(19) United States
(12) Reissued Patent
Schneider

(10) Patent Number: US RE48,867 E
(45) Date of Reissued Patent: Dec. 28, 2021

(54) BIOMETRIC MEDICAL ANTIFRAUD AND CONSENT SYSTEM

(71) Applicant: David Lyle Schneider, Hong Kong (CN)

(72) Inventor: David Lyle Schneider, Hong Kong (CN)

(73) Assignee: SCHNEIDER ADVANCED BIOMETRIC DEVICES LLC, Sheridan, WY (US)

(21) Appl. No.: 15/931,551

(22) Filed: May 13, 2020

Related U.S. Patent Documents

Reissue of:
(64) Patent No.: 10,468,129
Issued: Nov. 5, 2019
Appl. No.: 15/707,431
Filed: Sep. 18, 2017

U.S. Applications:
(60) Provisional application No. 62/395,514, filed on Sep. 16, 2016.

(51) Int. Cl.

| | |
|---|---|
| ***H04L 29/00*** | (2006.01) |
| ***G16H 10/60*** | (2018.01) |
| ***G06F 21/32*** | (2013.01) |
| ***G06F 21/62*** | (2013.01) |
| ***G06F 21/64*** | (2013.01) |
| ***H04L 9/06*** | (2006.01) |
| ***H04L 9/08*** | (2006.01) |
| ***H04L 9/32*** | (2006.01) |

(52) U.S. Cl.
CPC ..... *G16H 10/60* (2018.01); *G06F 21/32* (2013.01); *G06F 21/6245* (2013.01); *G06F 21/64* (2013.01); *H04L 9/06* (2013.01); *H04L 9/0866* (2013.01); *H04L 9/0894* (2013.01); *H04L 9/3231* (2013.01); *H04L 2209/88* (2013.01)

(58) Field of Classification Search
CPC ..... G16H 10/60; G06F 21/32; G06F 21/6245; G06F 21/64; H04L 9/06; H04L 9/0866; H04L 9/0894; H04L 9/3231; H04L 2209/88
See application file for complete search history.

(56) References Cited

U.S. PATENT DOCUMENTS 6,587,945 B1 * 7/2003 Pasieka ..... H04L 9/3236 713/176
6,882,859 B1 * 4/2005 Rao ..... G06F 3/023 455/550.1
7,305,562 B1 * 12/2007 Bianco ..... H04L 63/08 709/229
8,571,973 B1 * 10/2013 Haberaecker ..... G06Q 40/025 705/38
9,294,452 B1 * 3/2016 Jakobsson ..... H04L 63/08
(Continued)

*Primary Examiner* — Minh Dieu Nguyen
(74) *Attorney, Agent, or Firm* — Holly Li; Intelink Law Group, P.C.

(57) ABSTRACT

A specialized apparatus for recording medical transactions designed to protect patient privacy when necessary to record private biometric individual data. The mechanisms and proprietary methods scramble the biometric data within the recording device, unrecoverable when leaving recording device with high assurance, yet an audit copy can forward to outside permanent storage and systems.

18 Claims, 3 Drawing Sheets

AMENDED

(56) References Cited

U.S. PATENT DOCUMENTS

2004/0026496 A1* 2/2004 Zuili ..... G06Q 20/341 235/379
2004/0099731 A1* 5/2004 Olenick ..... G07F 17/26 235/380
2004/0104266 A1* 6/2004 Bolle ..... G06F 21/6245 235/382
2004/0208343 A1* 10/2004 Golden ..... A01K 11/008 382/110
2004/0246095 A1* 12/2004 Berger ..... G07C 9/00158 340/5.22
2006/0242423 A1* 10/2006 Kussmaul ..... G06F 21/32 713/182
2007/0177772 A1* 8/2007 Fujii ..... G06K 9/00906 382/115
2009/0304237 A1* 12/2009 Yoshikawa ..... G06K 9/00067 382/116
2010/0312548 A1* 12/2010 Herley ..... G06F 16/9032 704/9
2012/0158432 A1* 6/2012 Jain ..... G06Q 10/10 705/3
2012/0328171 A1* 12/2012 Vitt ..... G06K 9/00979 382/124
2013/0050652 A1* 2/2013 Wharton ..... H04N 5/2251 352/34
2013/0127909 A1* 5/2013 Nichols ..... G16H 30/40 345/638
2013/0179188 A1* 7/2013 Hyde ..... G16H 40/67 705/3
2013/0231954 A1* 9/2013 Bryant ..... G06F 21/32 705/3
2014/0046842 A1* 2/2014 Irudayam ..... G07F 19/202 705/43
2015/0223057 A1* 8/2015 Dellarciprete ..... H04L 67/10 455/410
2015/0235226 A1* 8/2015 Mao ..... G06Q 20/40145 705/72
2015/0321606 A1* 11/2015 Vartanian ..... B60R 1/00 348/148
2016/0026841 A1* 1/2016 Merrell ..... G06K 9/0002 382/124
2016/0241398 A1* 8/2016 Lewis ..... H04L 9/0891
2016/0364723 A1* 12/2016 Reese ..... G06Q 20/4012
2016/0364729 A1* 12/2016 Ruparelia ..... G06Q 20/40145
2017/0177855 A1* 6/2017 Costa Faidella ..... G06F 21/45
2017/0324750 A1* 11/2017 Khan ..... H04L 63/123

* cited by examiner

AMENDED

BIOMETRIC MEDICAL ANTIFRAUD AND CONSENT SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[CROSS-REFERENCE TO RELATED APPLICATIONS]

[This application claims benefit of 2016 provisional filing No. 62/395,514.]

BACKGROUND OF THE INVENTION

Medical device technology and the systems providing healthcare service to public populations have progressed exponentially during recent years following computing revolution in the early 1970's and personal computing revolutions since the 1980's.

This is well-known history and the public health benefits deriving from these technical and informational advancements are very important and significant for citizens of many countries. However, along with this progress, there are unanticipated challenges created by the complexity and interconnectedness of medical and healthcare industry systems.

One recent risk has been the proliferation of 'hacker' activity with purpose of causing damage and disruption to others based upon personal, political, nation-state and economic objectives. For medical industry, this means patients have valid concerns about the privacy, accuracy and disclosure of their very sensitive health-related and person-related 'information.'

Current industry trends address these problems with ubiquitous security solutions focused on applications, databases, firewalls, and activity alarm systems. One part of the solution is, for example, proprietary encrypting hard drives which are manufactured and installed in servers and workstations to protect against unauthorized disclosure. In 2017, there was a recent data breach at a major financial data collector resulting in over 140 million detailed financial records—data that will be used in theft and impersonation for fraudulent gain. So in short, this is a public problem that requires multiple solutions to protect privacy of individuals and patients. Privacy expectations are extremely sensitive in medical healthcare.

[BRIEF] SUMMARY [OF INVENTION]

[Purpose is to improve] *Embodiments of the present disclosure may support personal privacy, such as but not limited to* patient privacy, when using a biometric signature such as fingerprints, face scans and related characteristics [when] *to be* recorded into a computing system. A segregated and custom-purpose hardware device *is provided that* can scramble and encode private information in a manner that cannot be *easily* deciphered outside of the device. This therefore allows for permanent storage of such biometric information (*e.g.,* scrambled without external cipher keys) without *substantial* risk of viruses, theft and loss of system data from cloud, private network, or insurance industry data warehouse systems*, for example*. [Present invention claims]

*The present disclosure provides a* custom-purpose apparatus and methods, and [does] *need* not discuss the complex systematic and biometric workflow systems beyond the invention boundaries. [There] *Although a healthcare embodiment is provided for descriptive purposes, it shall be understood that there* are numerous possibilities[,] *and* variations[and vendors]*, such as* in the *insurance,* medical and finance [marketplace] *marketplaces, for the described and alternate embodiments* with biometric [reader equipment] *readers, without departing from the scope or spirit of the present disclosure.*

*An exemplary embodiment of the present disclosure provides a dedicated apparatus, which reads, records, and encodes patient biometric data, comprising mechanisms: inputting Last name, First name and Initial of patient; and inputting identifying Medical Number of patient; and inputting Date of Birth of patient in any format; and displaying countdown timer instructions for Photograph; and apparatus camera mechanism actuates Photograph, storing in temporary storage; and apparatus non-visible-light camera mechanism actuates Photograph, storing in temporary storage; and apparatus encoder chip combines and hashes two photographs into a combined data set; and camera encoder chip forwards combined data set (encoded private photos) to privacy encoder temporary storage; and apparatus displays instructions for fingerprint capture; and apparatus actuates fingerprint scan; and apparatus processes fingerprint scan into fingerprint template data set; and fingerprint encoder chip forwards combined data set (unencrypted fingerprint template data) to privacy encoder temporary storage; and privacy encoder communicates with device key chip delivering an encryption key unique to session recording; and privacy encoder mechanism combines and independently encrypts all data acquired including Last name, First name, Initial, encoded photograph data, encoded fingerprint template data into an encrypted data set; and apparatus purges all temporary data including unencrypted photograph, fingerprint scans, fingerprint templates; such that, the combined mechanisms delete original biometric data before delivery to a computing main board and software; and characterized in that, apparatus delivers resulting biometric data in an encoded and encrypted data set to a computing main board for permanent storage.*

*An exemplary embodiment of the present disclosure provides a hardware encryption device characterized in a compact, durable form comprising: camera module for visible-light photos; and non-visible-light camera module; where the two cameras align to photograph same direction; and fingerprint reader for one finger; and fingerprint reader module for multiple fingers, located proximate to the one finger reader; and chip that converts acquired photos into an encoded data set; and chip that converts acquired fingerprints in plurality into an encoded data set template; and device key chip processing a unique encoded symmetric device key; and hardware encryption processor; and wherein all modules are physically separated with hardware connection boundaries; and device physical separation precludes malicious virus software; such that only hardware encryption processor is connected to any computing main board.*

*An exemplary embodiment of the present disclosure provides a recording method within a compact device for a medical transaction declaration record, such that a real-time transaction encodes in a manner preventing forgery tampering, comprised of steps: device includes at least two fingerprint readers; when activated, device requires two immediate and simultaneous fingerprints; device display*

*prompts for camera photograph; device acquires camera photograph; device includes a hardware encryption module for encoding and encrypting of recorded record data; device inputs an "agreement document" (PDF) into device memory; device displays "agreement document" on device display; device records an affirmative or negative response through device display and user-selectable response; device prompts for biometric reader activation; device records biometric fingerprints from two persons, on two physical reader devices; device time-stamps each biometric fingerprints and electronically determines that fingerprints are recorded within 1000 ms (1 second); device computes an electronic decision about the physical proximity of one person and one witness based upon the first fingerprint reader time-stamp and the second fingerprint reader time-stamp; characterized by merging biometric signatures, from two persons, with an "agreement document," generating a "signed agreement document"; finally device outputs "signed agreement document" to a computing main board.*

*An exemplary embodiment of the present disclosure provides a computer-implemented recording method within a dedicated device for recording a medical transaction declaration record in real-time where a patient's private information is encoded and encrypted to prevent forgery tampering, the dedicated device including at least two biometric readers, a camera, a display screen, and an encryption module for encoding and encrypting record data in accordance with a private encryption key unique to the recording of the medical transaction declaration record, the method comprising: receiving an input of an agreement document and providing a visual display of the agreement document on the display screen; prompting for an affirmative or negative response from the patient through the display screen; activating the camera to capture a photograph of the patient; activating the biometric readers to record biometric fingerprint signatures of the patient and a witness; time-stamping and encoding the biometric fingerprint signatures into a machine-readable confirmation data set, and electronically determining that the biometric fingerprint signatures are recorded within 1000 ms (1 second); merging the biometric fingerprint signatures from the patient and the witness to generate a signed agreement document; and outputting the signed agreement document to computing main board, certified with the biometric fingerprint signatures of the patient and the witness.*

DETAILED DESCRIPTION OF INVENTION

Figure 1:
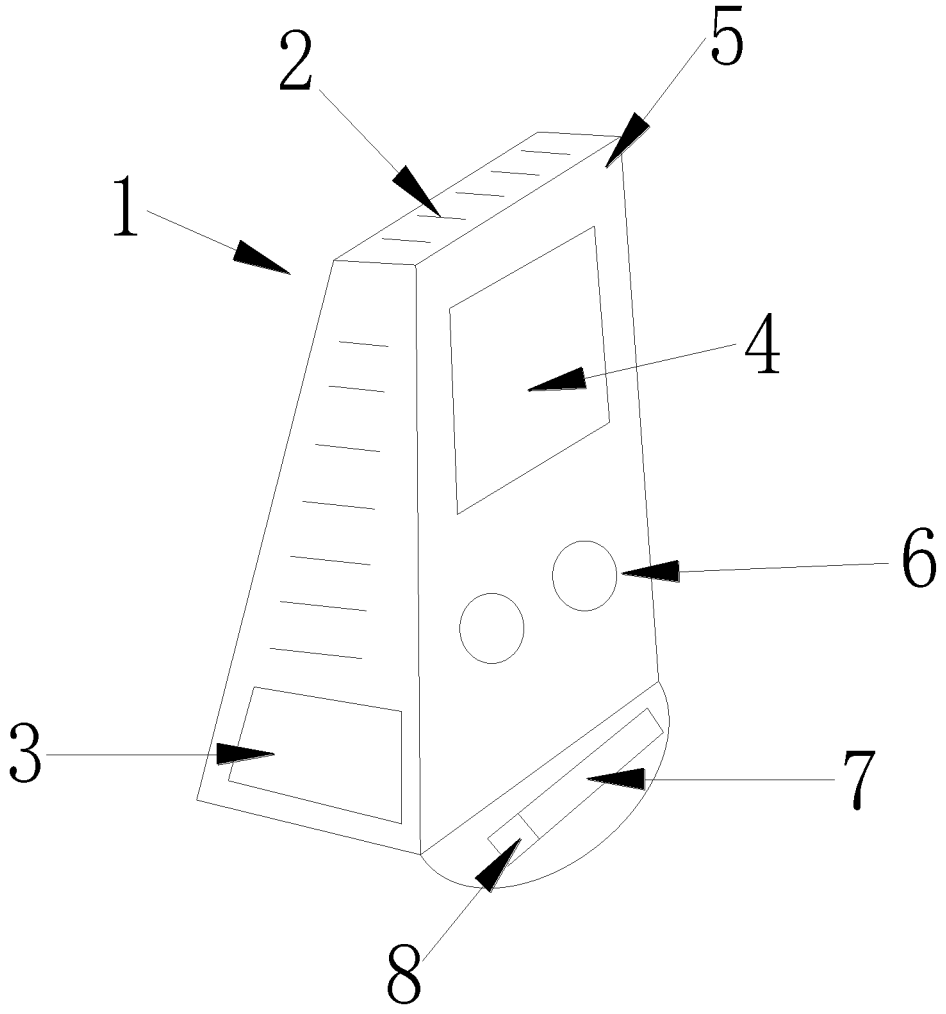
FIG. 1—Physical characteristics of preferred embodiment.
Figure 2:
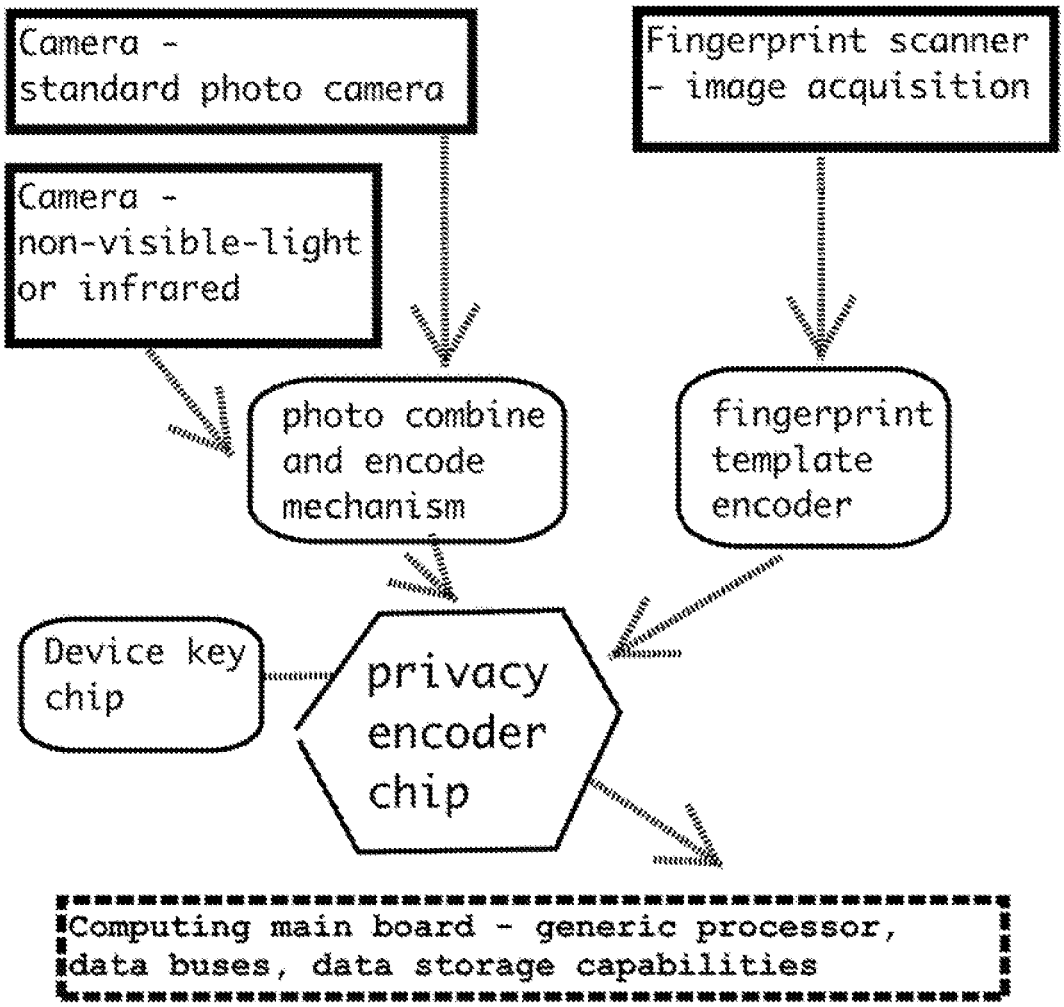
FIG. 2—Hardware mechanisms in recording apparatus.
Figure 3:
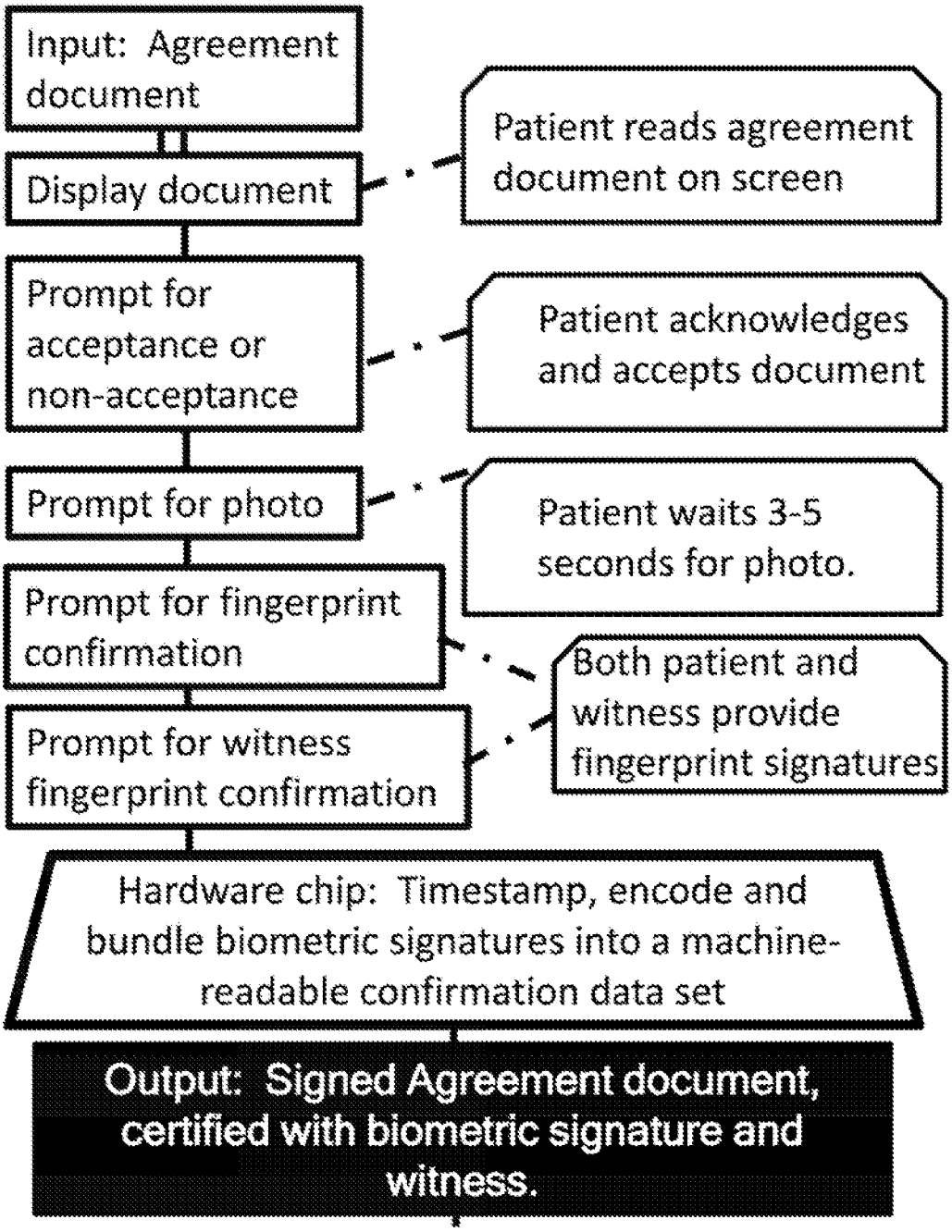
FIG. 3—Alternate embodiment functionality that records a real-time transaction for audit purpose.

Present invention is one highly-specific, specialized apparatus designed to protect patient privacy while recording some highly private and personal data about an individual. This is a challenging solution considering the high-level government and insurance industry goals, in a systematic way, demand collecting biometric information (i.e. fingerprints, photographs, other data based upon personal characteristics of an individual).

Present invention acknowledges necessity of positive identification readers which can improve safety and help audit the financial fraud abuses in a complex, multi-billion dollar industry.

Preceding technologies cited in the marketplace are fingerprint reader devices, biometric lock devices, access-authorization-auditing electronic system access controls, and numerous healthcare data processing systems and databases. Listing below includes general state of the prior art related to this subject: IBM thinkpad laptop integrated fingerprint readers.

Fingerprint reader hardware in law enforcement and customs identification, various.

Biometric door locks, various.

Systematic face scan, various.

Financial industry transaction systems, various.

NSA Type I, Type II hardware encryption, various.

DETAILED DESCRIPTION OF DRAWINGS

FIG. 1

(1) Sealed enclosure with filtered vents (2) Exhaust vent screen (3) Intake vent filter, necessary to remove particulate matter and improve reliability of device in imperfect and hot field conditions.

(4) Instructions display screen, 4×4 or various, displays written instructions provided to the patient.

(5) Metal heat-sink casing for camera heat.

(6) Camera module, normal visible light; and second Camera module, thermal, infrared or non-visible-light spectrum.

(7) Fingerprint bar reader, with multiple-finger scanning.

(8) Thumbprint reader, single-finger scanning.

FIG. 2

This diagram indicates the relationship and order of hardware mechanisms in the recorder device. The data flow begins at the top with an acquisition hardware, where raw biometric data is input. This unprotected data is encoded by hardware before delivery to temporary storage on an encryption chip mechanism. Device utilizes a private encryption key which is known only to the device. The hardware encryption mechanism is marked Privacy Chip to illustrate this final step.

FIG. 3

Alternate embodiment: This example chart demonstrates how a private biometric signature can be used to confirm a real-time medical transaction. For medical fraud prevention, these steps demonstrate how a patient can review a document and then certify with a witness, using a real-time apparatus, with hardware encryption.

I claim:

1. A computer-implemented recording method within a dedicated device for recording a medical transaction declaration record in real-time where a patient's private information is encoded and encrypted to prevent forgery *and* tampering, the dedicated device including at least two biometric readers, a camera, a display screen, and an encryption module for encoding and encrypting record data in accordance with a private encryption key unique to the recording of the medical transaction declaration record, the method comprising:

receiving an input of an agreement document and providing a visual display of the agreement document on the display screen;

prompting for an affirmative or negative response *to the agreement document* from the patient through the display screen;

activating the camera to capture a photograph of the patient;

*receiving personally identifiable information (PII) including a photograph of the patient;* activating the biometric readers to record biometric fingerprint signatures of the patient and a witness;

*acquiring a photographic image of the witness;*

*sensing biometric fingerprint signatures of the patient and the witness;*

*time-stamping the sensed biometric fingerprint signatures;* time-stamping and encoding the biometric fingerprint signatures into a machine-readable confirmation data set, and electronically determining that the biometric fingerprint signatures are recorded within [1000 ms (1 second)] *a predetermined time period, wherein electronically determining includes confirming that the time-stamped biometric fingerprint signatures were recorded within a preset time limit of each other*;

*determining a physical proximity of the patient and the witness based on the time-stamps of the biometric fingerprint signatures;*

*encoding the confirmed biometric fingerprint signatures into a machine-readable confirmation data set;* merging the biometric fingerprint signatures from the patient and the witness to generate a signed agreement document, *wherein merging the biometric fingerprint signatures includes merging the received PII with the encoded biometric fingerprint signatures to generate a biometrically signed electronic document*; [and]

outputting the signed agreement document to *a* computing main board, certified with the biometric fingerprint signatures of the patient and the witness, *wherein outputting the signed agreement document includes outputting the biometrically signed electronic document*.

*2. The method of claim 1, wherein the preset time limit is about one second.*

*3. The method of claim 1, further comprising:*

*acquiring a photographic image of the patient or the witness; and*

*merging the received PII with the acquired photographic image and the encoded biometric fingerprint signatures to generate the biometrically signed electronic document.*

*4. The method of claim 3, further comprising performing a facial recognition scan on the acquired photographic image.*

*5. The method of claim 1, further comprising:*

*acquiring a first visible-light image and a second non-visible light image of the patient; and*

*merging the received PII with the acquired first and second images and the encoded biometric fingerprint signatures to generate the biometrically signed electronic document.*

*6. The method of claim 5, further comprising:*

*combining the first image with the second image; and*

*encoding the combined image.*

*7. The method of claim 5, wherein the non-visible light image comprises infrared imagery.*

*8. The method of claim 1, further comprising:*

*prompting for a type of biometric reading;*

*recording a response through an apparatus display with user-selectable response for affirmation of the electronic document;*

*merging the recorded response and the biometric signatures from the patient and the witness into an electronic document to generate the signed electronic document.*

*9. The method of claim 8,*

*wherein the PII includes the patient's surname, given name, date of birth, and identifying number, and*

*wherein the response includes an affirmative response or a negative response for affirmation or disavowal of the electronic document, respectively.*

*10. The method of claim 1, further comprising:*

*displaying countdown timer instructions for acquiring photographs,*

*wherein the PII includes the photographs.*

*11. The method of claim 1, further comprising:*

*temporarily storing the PII and biometric information prior to outputting the biometrically signed electronic document; and*

*permanently deleting all temporarily stored information as it is used or output.*

*12. The method of claim 11, further comprising:*

*capturing a plurality of photographic images;*

*encoding the captured plurality of photographic images;*

*temporarily storing the encoded plurality of photograph images;*

*encrypting all data acquired including the PII, the encoded photograph data, and the biometric fingerprint signatures in accordance with a private encryption key unique to a session recording to generate an encrypted biometrically signed electronic document; and*

*purging all temporarily stored unencrypted data before outputting the encrypted biometrically signed electronic document.*

*13. The method of claim 1, further comprising:*

*displaying a proposed agreement document;*

*prompting the patient to acknowledge and accept the proposed agreement document with the patient's respective affirmative biometric fingerprint signature;*

*capturing a visible light image and a non-visible light image of the patient when sensing the affirmative biometric fingerprint signature of the patient;*

*time-stamping and privacy-encoding the captured images and the affirmative biometric fingerprint signatures of the patient and the witness into a machine-readable confirmation data set; and*

*merging the proposed agreement document with the time-stamped privacy-encoded images and affirmative biometric fingerprint signatures to generate a signed agreement document memorialized or certified with the images and affirmative biometric fingerprint signatures.*

*14. An apparatus for recording an electronic document including personally identifiable information (PII), comprising:*

*an input device for receiving PII from a person;*

*a sensor device for sensing affirmative biometric fingerprint signatures of the person and a witness;*

*a clock device for time-stamping the sensed biometric fingerprint signatures;*

*a validation device for confirming that the time-stamped biometric fingerprint signatures were recorded within a preset time limit of each other;*

*a proximity measuring device for determining a physical proximity of the person and the witness based on the time-stamps of the affirmative biometric fingerprint signatures;*

*an encoder for encoding the confirmed biometric fingerprint signatures into a machine-readable confirmation data set;*

*a collecting device for merging the received PII with the encoded biometric fingerprint signatures to generate a biometrically signed electronic document; and*

*an output device for outputting the biometrically signed electronic document.*

*15. The apparatus of claim 14, wherein the apparatus is a dedicated device for recording the electronic document comprising a medical transaction declaration record in real-time, the person is a patient, and the PII includes the patient's private medical information, the apparatus further comprising:*

*an encryption device for encrypting the biometrically signed electronic document to prevent forgery, tampering, or accidental disclosure.*

*16. The apparatus of claim 14, further comprising:*

*a plurality of biometric fingerprint readers;*

*at least one camera;*

*a display screen; and*

*an encryption module for encoding and encrypting the electronic document in accordance with a private encryption key unique to the biometrically signed electronic document.*

*17. The apparatus of claim 14, wherein the electronic document is a proposed agreement document between the person and the witness, the apparatus further comprising:*

*a display unit for providing a visual display of the proposed agreement document;*

*an acceptance device for receiving an affirmative or negative response from each of the person and the witness responsive to the display means as to acceptance of the proposed agreement document.*

*18. The apparatus of claim 14, wherein the preset time limit is about one second.*

* * * * *